(12) United States Patent
Singh et al.

(10) Patent No.: US 9,932,336 B2
(45) Date of Patent: Apr. 3, 2018

(54) PROCESS FOR THE PREPARATION OF APIXABAN AND INTERMEDIATES THEREOF

(71) Applicant: JUBILANT GENERICS LIMITED, Noida, Uttar Pradesh (IN)

(72) Inventors: Khushwant Singh, Noida (IN); Amit Kumar Srivastava, Noida (IN); Ratnakar Tripathi, Noida (IN); Jai Prakash Verma, Noida (IN); Dharam Vir, Noida (IN); Lalit Kumar, Noida (IN); Mukesh Masand, Noida (IN); Rajendra Singh Shekhawat, Noida (IN); Rakesh Tiwari, Noida (IN); Sujay Biswas, Noida (IN)

(73) Assignee: JUBILANT GENERICS LIMITED, Noida (IN)

( * ) Notice: Subject to any disclaimer, the term of this patent is extended or adjusted under 35 U.S.C. 154(b) by 0 days.

(21) Appl. No.: 15/522,758

(22) PCT Filed: Oct. 20, 2015

(86) PCT No.: PCT/IN2015/050138
§ 371 (c)(1),
(2) Date: Apr. 27, 2017

(87) PCT Pub. No.: WO2016/067308
PCT Pub. Date: May 6, 2016

(65) Prior Publication Data
US 2017/0313699 A1 Nov. 2, 2017

(30) Foreign Application Priority Data
Oct. 28, 2014 (IN) .......................... 3063/DEL/2014

(51) Int. Cl.
*A61K 31/437* (2006.01)
*C07D 401/14* (2006.01)
*C07D 471/04* (2006.01)
*C07D 213/74* (2006.01)

(52) U.S. Cl.
CPC ......... *C07D 471/04* (2013.01); *C07D 213/74* (2013.01)

(58) Field of Classification Search
CPC ........................... C07D 401/14; A61K 31/437
USPC .......................................... 546/119; 514/303
See application file for complete search history.

(56) References Cited

U.S. PATENT DOCUMENTS

| 6,919,451 B2 | 7/2005 | Zhou et al. |
| 6,967,208 B2 | 11/2005 | Pinto et al. |
| 7,396,932 B2 | 7/2008 | Shapiro et al. |

FOREIGN PATENT DOCUMENTS

| CN | 101967145 A | 2/2011 |
| WO | 2014044107 | * 3/2014 |

OTHER PUBLICATIONS

Organic Syntheses, Coll. vol. 3, p. 82 (1955); vol. 25, p. 5 (1945); by W W Hartman et.al. fig 1 and procedure.
Organic Syntheses, Coll. vol. 3, p. 63 (1955); vol. 22, p. 9 (1942) by C. F. H. Allen et.al. DOI: 10.15227 orgsyn.022.0009 fig 1 and procedure.

* cited by examiner

*Primary Examiner* — Niloofar Rahmani
(74) *Attorney, Agent, or Firm* — Maschoff Brennan

(57) ABSTRACT

The present invention relates to an improved process for the preparation of Apixaban and intermediates thereof. Further the present invention also relates to novel intermediate of Formula V and its process for the preparation.

13 Claims, No Drawings

PROCESS FOR THE PREPARATION OF APIXABAN AND INTERMEDIATES THEREOF

FIELD OF THE INVENTION

The present invention relates to an improved process for the preparation of Apixaban and intermediates thereof. The present invention also relates to novel intermediate of Formula V, used in the preparation of Apixaban.

BACKGROUND OF THE INVENTION

Apixaban is chemically known as 1-(4-methoxyphenyl)-7-oxo-6-[4-(2-oxopiperidin-1-yl) phenyl]-4,5,6,7-tetrahydro-1H-pyrazolo[3,4-c]pyridine-3-carboxamide and represented by following structural Formula I,

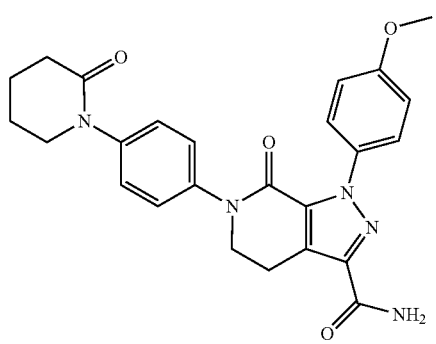

Formula I

Apixaban (BMS-562247-01) is an anticoagulant used for the prevention of venous thromboembolism and venous thromboembolic events. Apixaban is marketed under the trade name "Eliquis" and is being developed in a joint venture by Pfizer and Bristol-Myers Squibb.

U.S. Pat. No. 6,967,208 specifically discloses Apixaban and its process, which comprises reaction of 4-iodoaniline with 5-bromovaleryl chloride to give lactam intermediate, which is further dissolved in chloroform and reacted with phosphorus pentachloride, quenched with water and condensed with morpholine to give 1-(4-iodophenyl)-3-morpholino-5,6-dihydropyridin-2(1H)-one. The obtained 1-(4-iodophenyl)-3-morpholino-5,6-dihydropyridin-2(1H)-one is reacted with ethyl (Z)-2-chloro-2-(2-(4-methoxyphenyl)hydrazono)acetate to give ethyl 6-(4-iodophenyl)-1-(4-methoxyphenyl)-7-oxo-4,5,6,7-tetrahydro-1H-pyrazolo[3,4-c]pyridine-3-carboxylate. The resulted compound undergone Ullmann Reaction with piperidin-2-one in presence of CuI, potassium carbonate at 130° C. for 24 hours to give ethyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate, which is subsequently amidated by ammonia solution in ethylene glycol to give Apixaban. The reaction sequence of above patent is illustrated in scheme 1.

Scheme 1
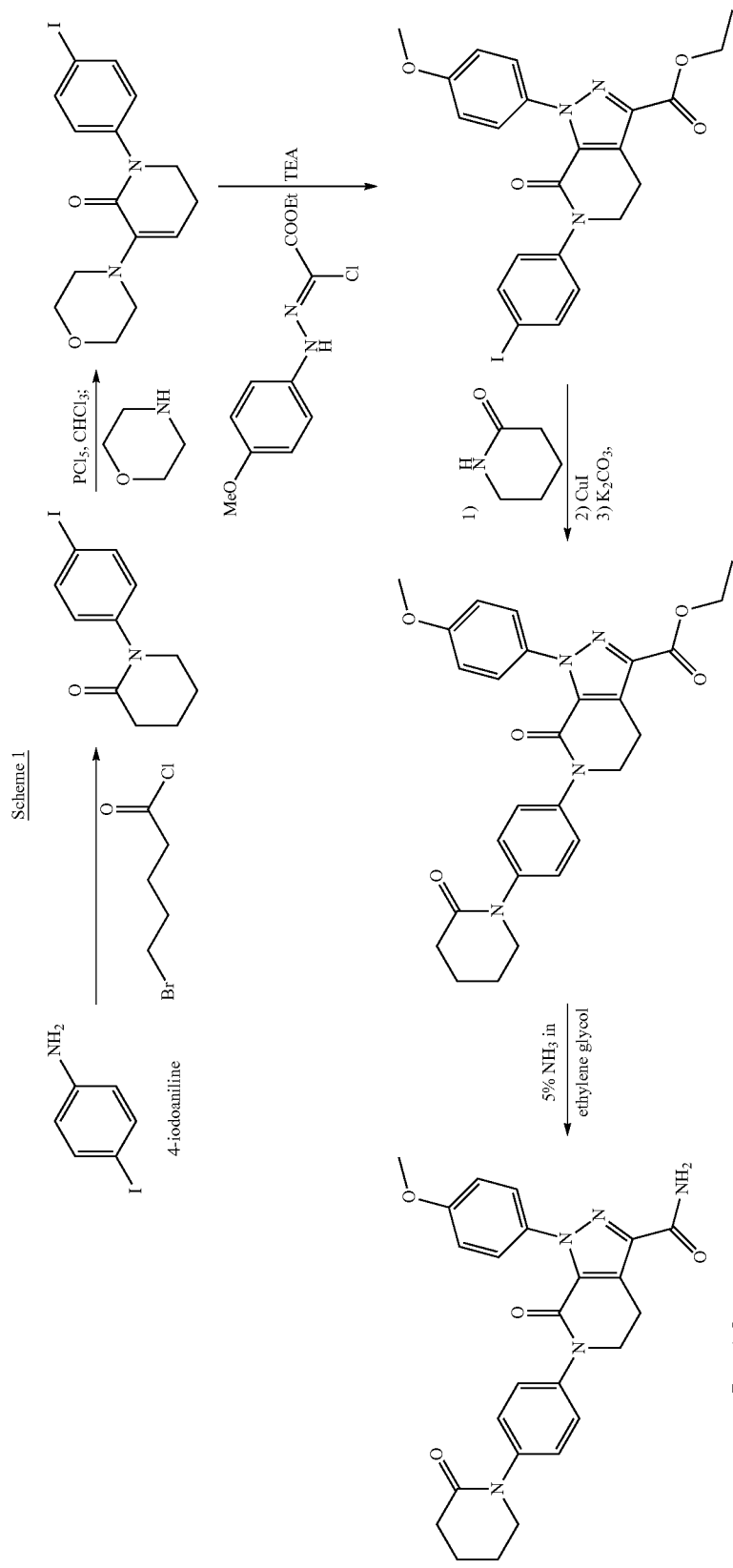
Formula I

U.S. Pat. No. 6,919,451 discloses another process for the preparation of Apixaban, which comprises reaction of piperidin-2-one with phosphorus trichloride, treated with lithium carbonate and condensed with morpholine to give 3-morpholino-5,6-dihydropyridin-2(1H)-one. The obtained 3-morpholino-5,6-dihydropyridin-2(1H)-one is reacted with ethyl (Z)-2-chloro-2-(2-(4-methoxyphenyl)hydrazono)acetate in the presence of base to give ethyl 1-(4-methoxyphenyl)-7a-morpholino-7-oxo-3a,4,5,6,7,7a-hexahydro-1H-pyrazolo[3,4-c]pyridine-3-carboxylate, which is further treated with trifluoroacetic acid to give ethyl 1-(4-methoxyphenyl)-7-oxo-3a,4,5,6,7,7a-hexahydro-1H-pyrazolo[3,4-c]pyridine-3-carboxylate. The resulting compound was undergone Ullmann reaction with 1-(4-iodophenyl)piperidin-2-one in presence of CuI, potassium carbonate at 125° C. for 10 hours to give 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylic acid, which is subsequently reacted with isobutyl chloroformate and ammonium hydroxide in the presence of triethylamine to give Apixaban. The reaction sequence of above patent is illustrated in scheme 2.

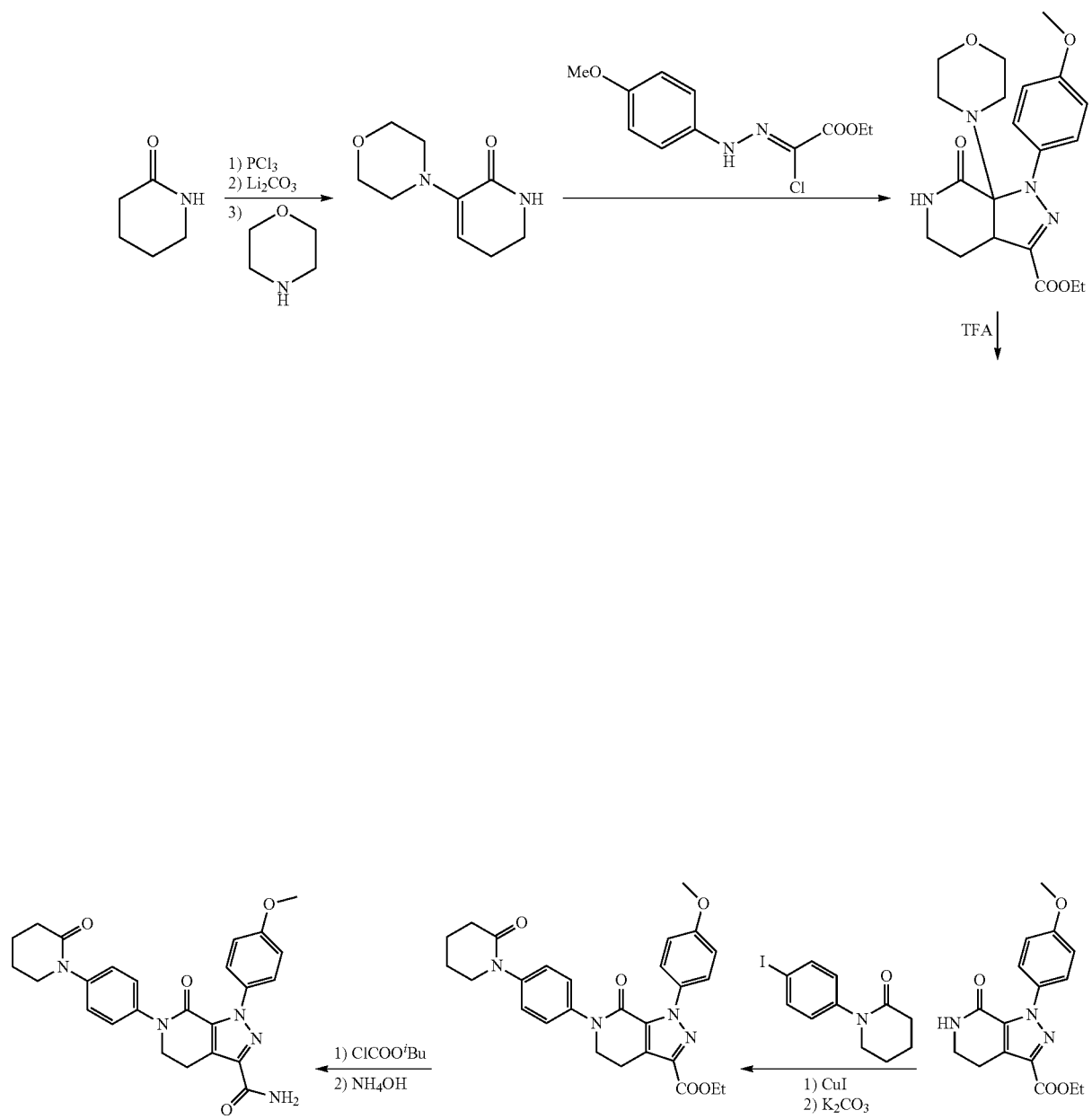

Scheme 2

Formula I

The main drawbacks of the above processes are the use of laborious column chromatographic purification at multiple stages, which not only increases the consumption of solvent but also difficult to handle on the commercial scale, including the obvious practical limitations of column chromatography on industrial scale. Also the present process uses Ullmann Reaction which requires harsh condition i.e. heating the reaction mixture at 125-130° C. for up to 24 hours in the presence of Copper (I) catalyst, which is difficult to operate on the large scale. Furthermore, the yield at the intermediate stage is very low (~21%) which makes the process uneconomical and industrially unviable.

U.S. Pat. No. 7,396,932 discloses process for the preparation of Apixaban, which comprises reaction of 3-chloro-1-(4-nitrophenyl)-5,6-dihydropyridin-2(1H)-one with ethyl (Z)-2-chloro-2-(2-(4-methoxyphenyl)hydrazono)acetate in the presence of base to give ethyl 1-(4-methoxyphenyl)-6-(4-nitrophenyl)-7-oxo-4,5,6,7-tetrahydro-1H-pyrazolo[3,4-c]pyridine-3-carboxylate. The nitro group of the resulting compound was reduced and reacted with 5-halovaleryl chloride wherein halogen can be selected from chloro or bromo to give ethyl 6-(4-(5-halopentanamido)phenyl)-1-(4-methoxyphenyl)-7-oxo-4,5,6,7-tetrahydro-1H-pyrazolo[3,4-c]pyridine-3-carboxylate. It is further cyclized to give ethyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate. The obtained compound was subsequently amidated by formamide in the presence of dehydrating agent to give Apixaban. The reaction sequence of above patent is illustrated in scheme 3.

Scheme 3

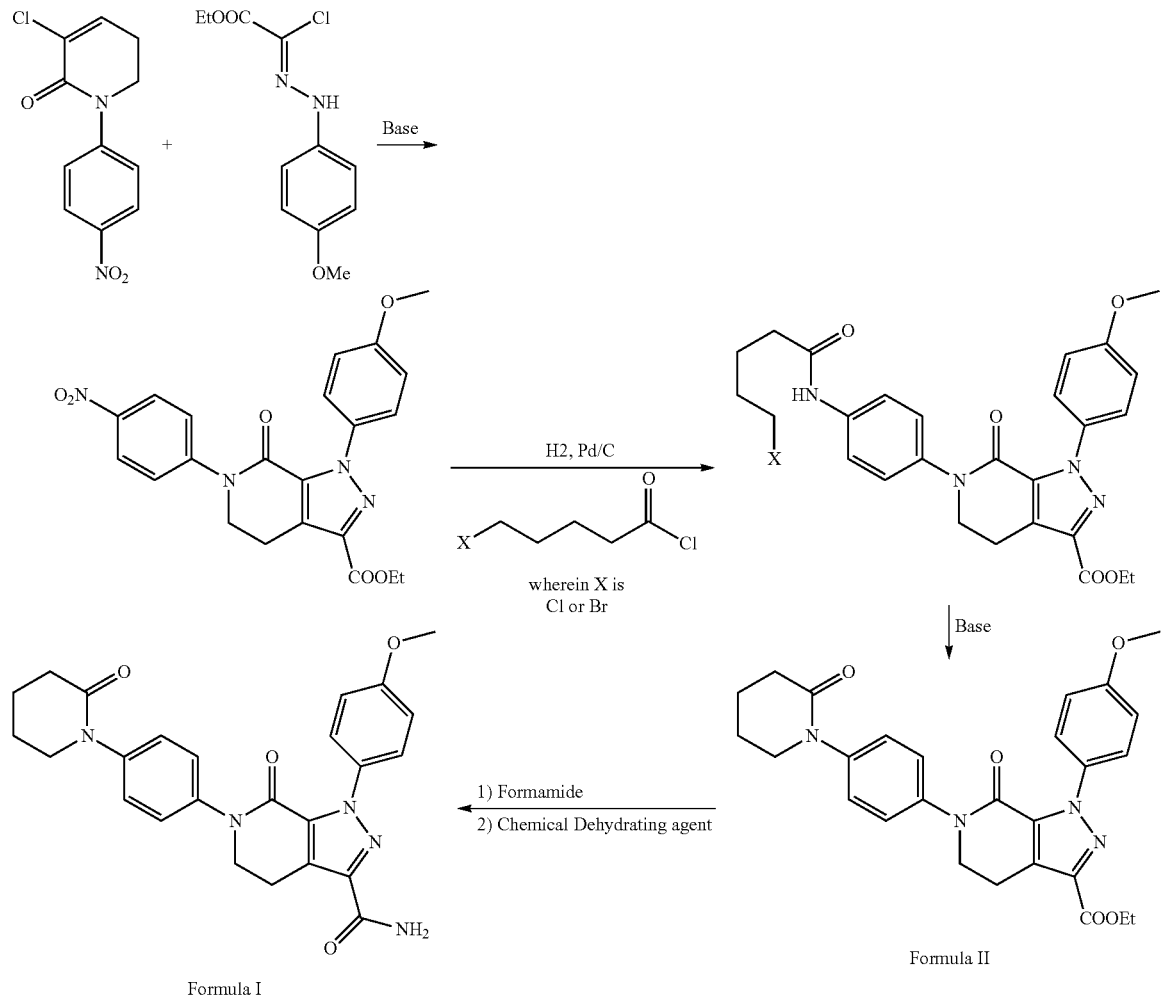

Formula I

Formula II

CN patent No. 101967145B discloses preparation of Apixaban, which comprises reduction of 1-(4-nitrophenyl)-3-morpholino-5,6-dihydropyridin-2(1H)-one with sodium sulfide to give 1-(4-aminophenyl)-3-morpholino-5,6-dihydropyridin-2(1H)-one which further coupled with 5-chlorovaleryl chloride in the presence of organic base, followed by in-situ cyclization to give 3-morpholino-1-(4-(2-oxopiperidin-1-yl)phenyl)-5,6-dihydropyridin-2(1H)-one. The resulting compound was reacted with ethyl (Z)-2-chloro-2-(2-(4-methoxyphenyl)hydrazono)acetate in the presence of alkali metal iodide as a catalyst and triethylamine, followed by treatment with aqueous HCl to give ethyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate. The resulting compound was amidated by ammonia/water to give Apixaban. The main drawback of the process is the use of sodium sulfide and alkali metal catalyst which is hazardous and makes the process environmental unfriendly. The reaction sequence of above patent is illustrated in scheme 4.

Scheme 4
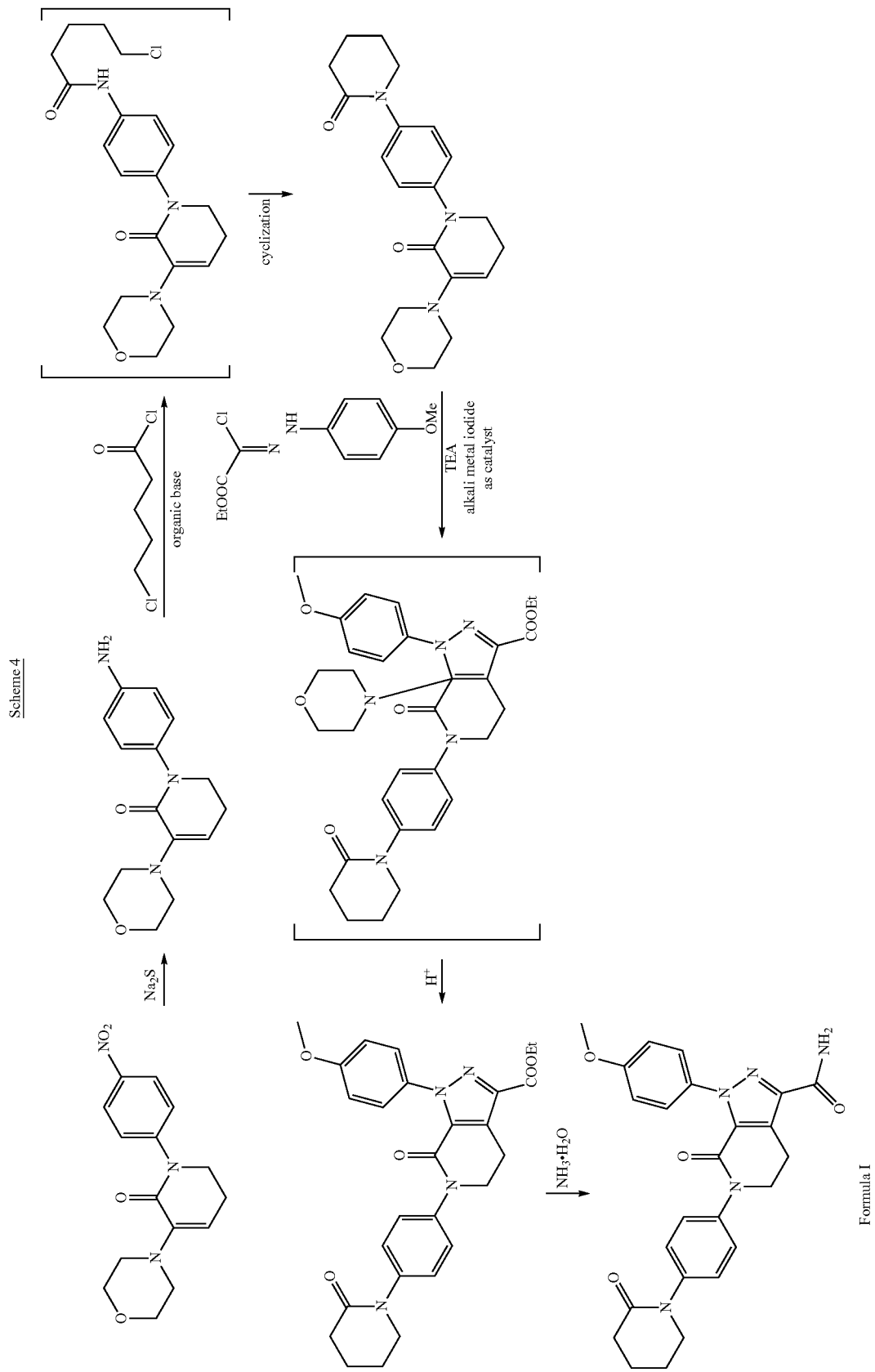

The processes disclosed in the above mentioned prior art(s) are having several limitations like multiple chemical steps, overall low yields, use of column chromatography, use of expensive and toxic reagents etc.

Thus, there is a need to develop a simple, economically viable, industrially feasible and environmental friendly process for the preparation of Apixaban, which overcomes the drawback of the above mentioned prior arts.

OBJECT AND SUMMARY OF THE INVENTION

The principal object of the present invention is to provide an improved process for the preparation of Apixaban, which alleviates the drawbacks of prior art processes and provide an alternative process for the preparation of Apixaban.

It is another object of the present invention to provide a cost effective and industrially feasible process for the preparation of Apixaban, which minimizes the formation of by products and gives Apixaban in high yield and purity.

It is still another object of the present invention to provide an improved and commercially viable process for the preparation of Apixaban via novel intermediate of Formula V.

In one general aspect, the present invention is directed to a process for preparation of Apixaban of Formula I comprising the steps of:

a) reducing 3-morpholino-1-(4-nitrophenyl)-5,6-dihydropyridin-2(1H)-one of Formula II in presence of reducing agent to give 3-morpholino-1-(4-aminophenyl)-5,6-dihydropyridin-2(1H)-one of Formula III;

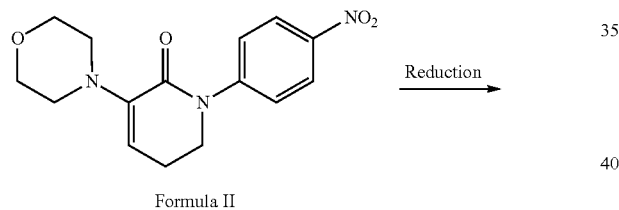

Formula II

Reduction

Formula III b) reacting 3-morpholino-1-(4-aminophenyl)-5,6-dihydropyridin-2(1H)-one of Formula III with compound of Formula IV in presence of base and solvent to give compound of Formula V,

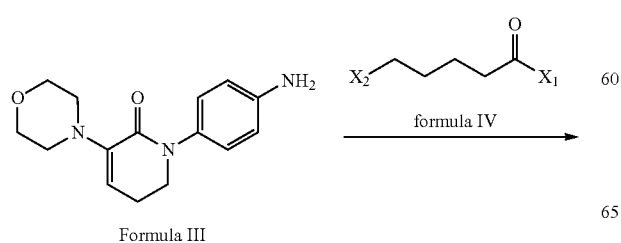

Formula III formula IV

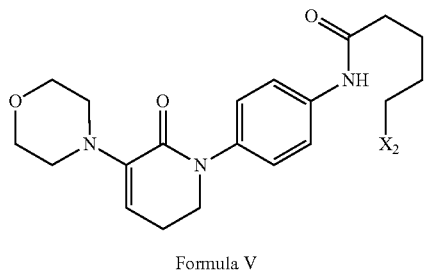

Formula V wherein, $X_1$ is selected from chloro, bromo, iodo or alkyl carboxy, wherein alkyl is selected from ethyl, isobutyl, t-butyl and the like; and $X_2$ is selected from leaving group such as, chloro, bromo, iodo, mesylate, substituted or unsubstituted phenyl sulfonate and the like.

c) cyclizing compound of Formula V in presence of base and solvent to give 3-morpholino-1-(4-(2-oxopiperidin-1-yl)phenyl)-5,6-dihydropyridin-2(1H)-one of Formula VI;

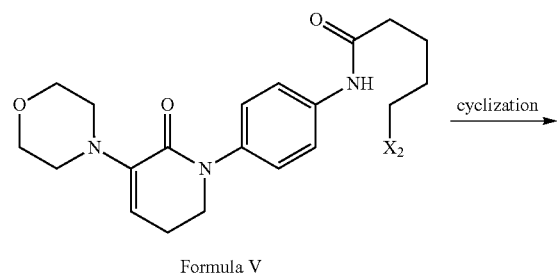

Formula V cyclization

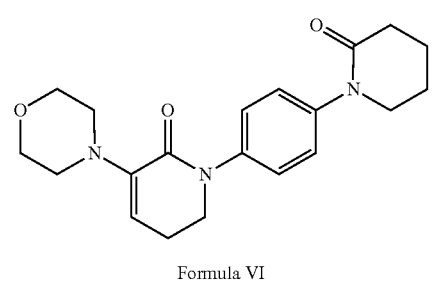

Formula VI where $X_2$ is defined as above;

d) condensing 3-morpholino-1-(4-(2-oxopiperidin-1-yl)phenyl)-5,6-dihydropyridin-2(1H)-one of Formula VI with alkyl-(Z)-2-halo-2-(2-(4-methoxyphenyl)hydrazono)acetate of Formula VII, wherein $X_1$ is selected from chloro, bromo, iodo; in presence of base and solvent followed by treatment with suitable acid to give alkyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate of Formula VIII;

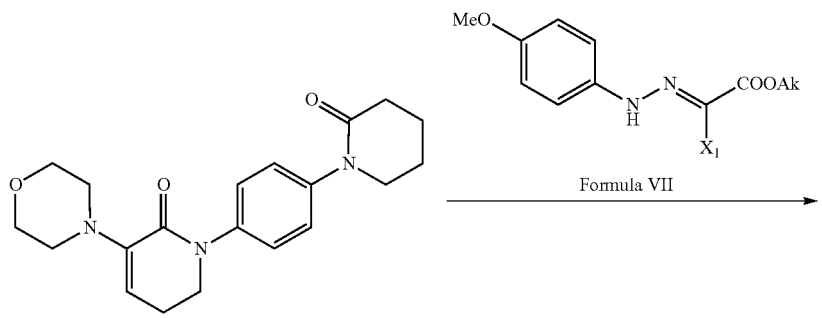

Formula VI

Formula VII

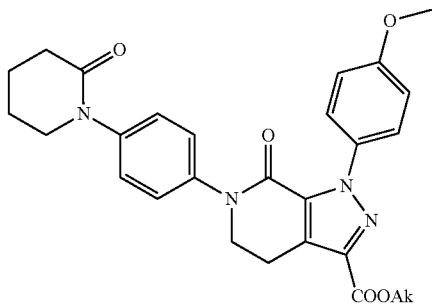

Formula VIII e) amidating the resulting compound Formula VIII using formamide in presence of base to give Apixaban of Formula I;

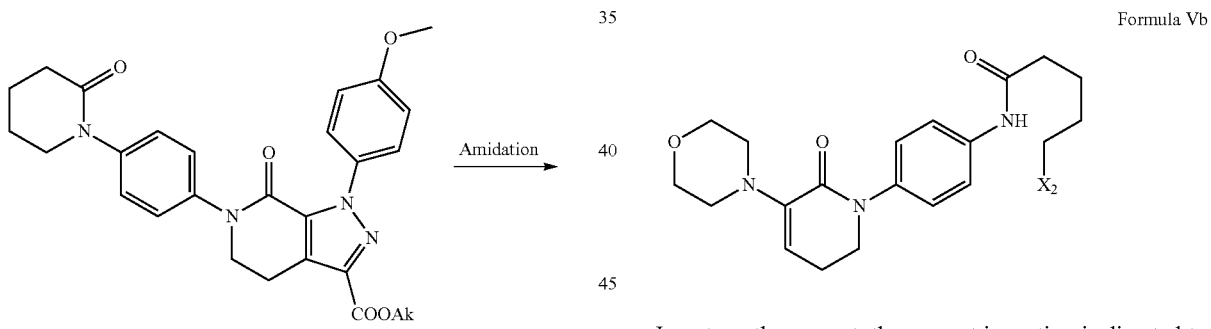

Formula VIII

Apixaban
Formula I f) optionally purifying Apixaban of Formula I.

In another aspect, the present invention is directed to a compound of Formula Vb, wherein $X_2$ is selected from leaving group such as bromo, iodo, mesylate, substituted or unsubstituted phenyl sulfonate and the like.

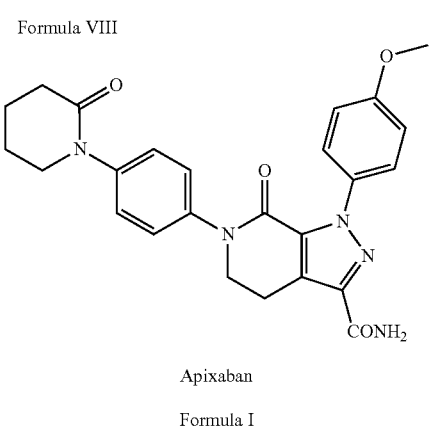

Formula Vb

In yet another aspect, the present invention is directed to a process for the preparation of compound of Formula Vb by reacting 3-morpholino-1-(4-aminophenyl)-5,6-dihydropyridin-2(1H)-one of Formula III with compound of Formula IV, wherein $X_1$ is selected from chloro, bromo, iodo or alkyl carboxy, wherein alkyl is selected from ethyl, isobutyl, t-butyl and the like; $X_2$ is selected from leaving group such as bromo, iodo, mesylate, substituted or unsubstituted phenyl sulfonate and the like.

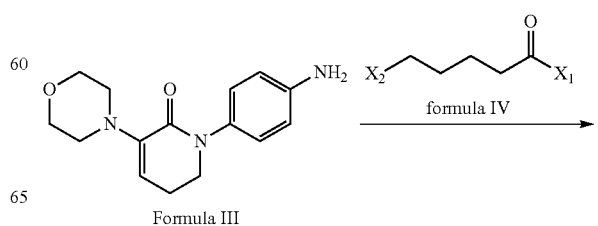

Formula III formula IV

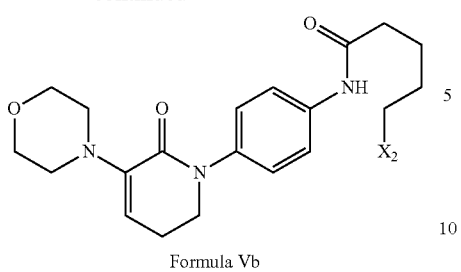

Formula Vb

In still another aspect, the present invention is directed to a process for the preparation of compound of Formula Vb by reacting of 3-morpholino-1-(4-aminophenyl)-5,6-dihydropyridin-2(1H)-one of Formula III with compound of Formula IV in the presence of base and solvent; wherein $X_1$ is selected from chloro, bromo, iodo or alkyl carboxy, wherein alkyl is selected from ethyl, isobutyl, t-butyl and the like; $X_2$ is selected from leaving group such as bromo, iodo, mesylate, substituted or unsubstituted phenyl sulfonate and the like.

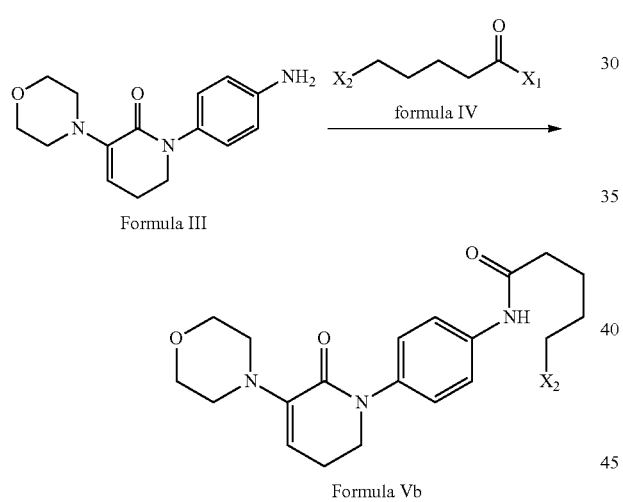

Formula III formula IV

Formula Vb

It is still another aspect of the present invention, to provide Apixaban substantially free from impurities and residual solvents.

DETAILED DESCRIPTION OF THE INVENTION

While this specification concludes with claims particularly pointing out and distinctly claiming that, which is regarded as the invention, it is anticipated that the invention can be more readily understood through reading the following detailed description of the invention and study of the included examples.

According to one aspect, the present invention is directed to a process for preparation of Apixaban of Formula I, comprising the steps of:

a) reducing 3-morpholino-1-(4-nitrophenyl)-5,6-dihydropyridin-2(1H)-one of Formula II in presence of reducing agent to give 3-morpholino-1-(4-aminophenyl)-5,6-dihydropyridin-2(1H)-one of Formula III;

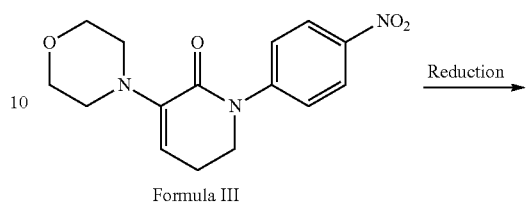

Formula III

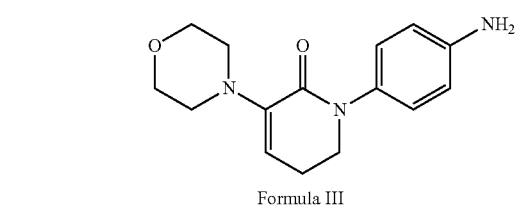

Formula III b) reacting 3-morpholino-1-(4-aminophenyl)-5,6-dihydropyridin-2(1H)-one of Formula III with compound of Formula IV in presence of base and solvent to give compound of Formula V;

formula IV

Formula III

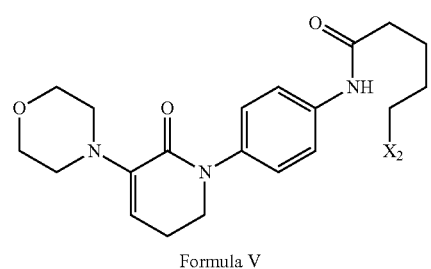

Formula V wherein, $X_1$ is selected from chloro, bromo, iodo or alkyl carboxy, wherein alkyl is selected from ethyl, isobutyl, t-butyl and the like; and $X_2$ is selected from leaving group such as, chloro, bromo, iodo, mesylate, substituted or unsubstituted phenyl sulfonate and the like;

c) cyclizing compound of Formula V in presence of base and solvent to give 3-morpholino-1-(4-(2-oxopiperidin-1-yl)phenyl)-5,6-dihydropyridin-2(1H)-one of Formula VI;

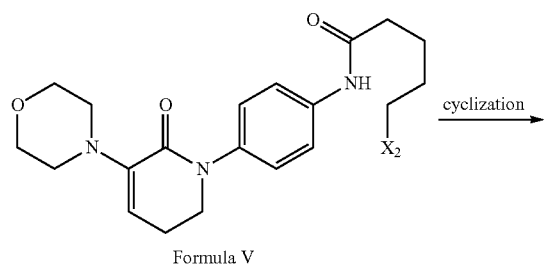

Formula V

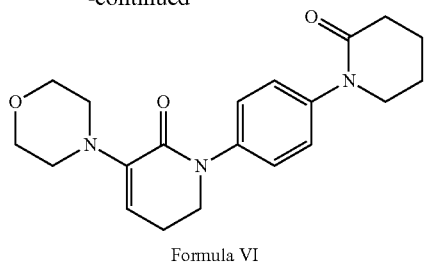

Formula VI where $X_2$ is defined as above;

d) condensing 3-morpholino-1-(4-(2-oxopiperidin-1-yl)phenyl)-5,6-dihydropyridin-2(1H)-one of Formula VI with alkyl-(Z)-2-halo-2-(2-(4-methoxyphenyl)hydrazono)acetate of Formula VII, wherein $X_1$ is selected from chloro, bromo, iodo; and Ak is selected from H, $C_1$-$C_6$ alkyl group; in presence of a base and solvent followed by treatment with suitable acid to give alkyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate of Formula VIII;

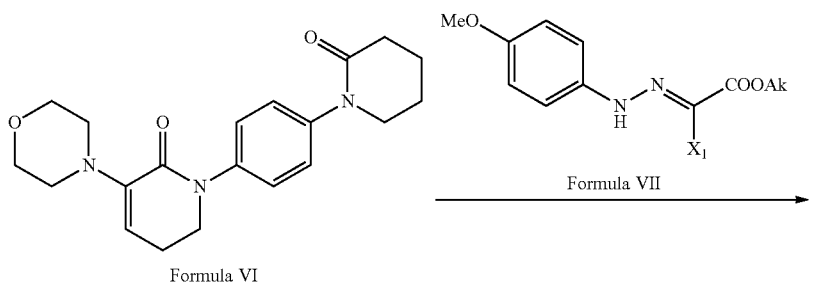

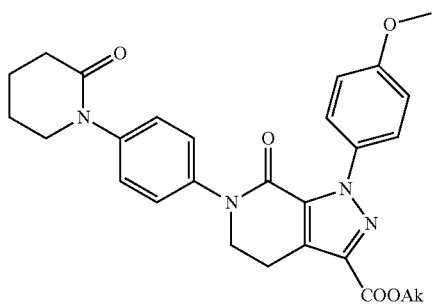

Formula VIII e) amidating the resulting compound of Formula VIII using formamide in presence of base to give Apixaban of Formula I;

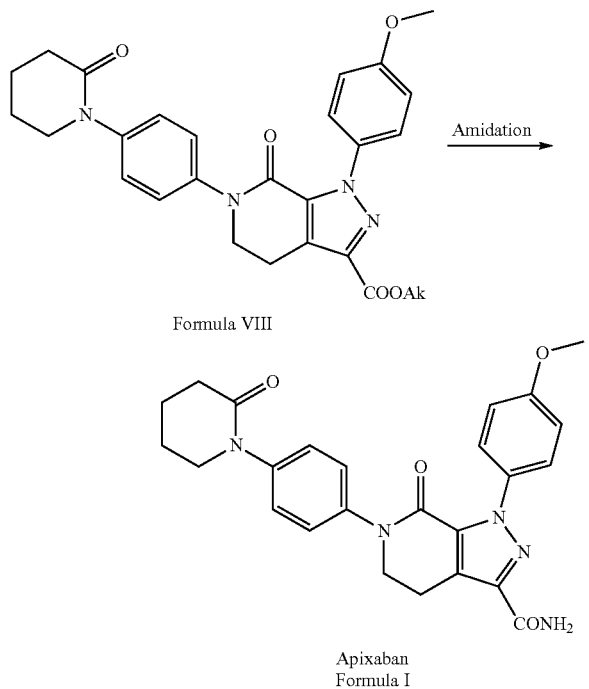

Formula VIII

Apixaban
Formula I f) optionally purifying Apixaban of Formula I.

Processes for obtaining 3-morpholino-1-(4-nitrophenyl)-5,6-dihydropyridin-2(1H)-one of Formula II, can be according to literature methods.

According to the present invention, step (a) involves reduction of 3-morpholino-1-(4-nitrophenyl)-5,6-dihydropyridin-2(1H)-one of Formula II with reducing agent in suitable solvent to obtain 3-morpholino-1-(4-aminophenyl)-5,6-dihydropyridin-2(1H)-one of Formula III.

The reducing agent used in step (a) may be selected from the group comprising of hydrogen in presence of metal catalysts such as Pd/C, Pt/C, Raney Ni optionally in presence of ethanolamine or hydrazine hydrate, transfer hydrogenation using ammonium formate, formic acid in presence of metal catalyst such as Pd/C, Pt/C; Fe/HCl, Zn/HCl, Sn/HCl, or pyridinium zinc complex; sodium borohydride, sodium cyanoborohydride, sodium triacetoxyborohydride, trihalosilanes, diisobutylaluminium hydride (DIBAL), lithium triethylborohydride, lithium tri-sec-butyl borohydride (L-selectride), trialkylsilanes optionally in combination with trifluoroacetic acid.

The suitable solvent for reduction is selected from the group comprising of alcohols such as methanol, ethanol, propanol, isopropanol and butanol and the like; chlorinated hydrocarbons such as methylene chloride, chloroform and the like; ethers such as diisopropyl ether, methyl tent-butyl ether, dioxane, tetrahydrofuran and the like; esters such as ethyl acetate, isopropyl acetate and the like, polar aprotic solvents such as dimethylformamide, dimethyl sulfoxide, N-methylpyrrolidone, and water or mixture thereof.

According to the present invention, step (b) involves reacting 3-morpholino-1-(4-aminophenyl)-5,6-dihydropyridin-2(1H)-one of Formula III with compound of Formula IV, wherein, $X_1$ is selected from chloro, bromo, iodo or alkyl carboxy, wherein alkyl is selected from ethyl, isobutyl, t-butyl and the like; and $X_2$ is selected from leaving group such as, chloro, bromo, iodo, mesylate, substituted or unsubstituted phenyl sulfonate and the like, which can be carried out in presence of suitable base and solvent to give compound of Formula V.

In an embodiment, compound of Formula IV can be selected from 5-bromopentanoyl chloride, 5-iodopentanoyl chloride, 5-bromopentanoyl bromide, 5-iodopentanoyl iodide, 5-chlorovaleroyl chloride and the like.

The suitable base used herein is selected from inorganic or organic base. The inorganic base is selected from the group comprising of alkali metal or alkaline earth metal carbonates, bicarbonates, hydroxides and the like, wherein the alkali metal and alkaline earth metal is selected from a group comprising of lithium, sodium, potassium, magnesium, calcium, cesium, barium, and the like. The organic base is selected from the group comprising of triethylamine, diisopropylamine, diisopropylethylamine, piperidine, pyridine N-methyl morpholine N,N-dimethylbenzylamine, picoline, lutidine and the like.

The suitable solvent is selected from the group comprising of chlorinated hydrocarbons such as methylene chloride, chloroform and the like; ethers such as diisopropyl ether, methyl tert-butyl ether, dioxane, tetrahydrofuran and the like; esters such as ethyl acetate, isopropyl acetate and the like, hydrocarbon such as toluene, n-heptane, cyclohexane, xylene; polar aprotic solvents such as dimethylformamide, dimethyl sulfoxide, N-methylpyrrolidone or mixture thereof.

According to the present invention, step (c) involves cyclization of compound of Formula V in the presence of suitable base and solvent to give 3-morpholino-1-(4-(2-oxopiperidin-1-yl)phenyl)-5,6-dihydropyridin-2(1H)-one of Formula VI.

The suitable base used herein is selected from metal alkoxide, inorganic or organic base. The metal alkoxide used is selected from alkali metal or alkaline earth metal salt of alcohols, wherein the alkali metal and alkaline earth metal is selected from a group comprising of lithium, sodium, potassium, magnesium, calcium, cesium, barium, and the like and alcohol is selected from methanol, ethanol, propanol, butanol, pentanol and the like. The inorganic base is selected from the group comprising of alkali metal or alkaline earth metal carbonates, bicarbonates, hydroxides amides of lithium, sodium, potassium, magnesium, calcium, cesium, barium and the like. The organic base is selected from the group comprising of triethylamine, diisopropylamine, diisopropylethylamine, 1,4-diazabicyclo[2.2.2]octane, 1, 8-diazabicyclo [5.4.0]undec-7-ene, piperidine, pyridine N-methyl morpholine N,N-dimethylbenzylamine, picoline, lutidine and the like.

The suitable solvent for above reaction is selected from the group comprising of chlorinated hydrocarbons such as methylene chloride, chloroform and the like; ethers such as diisopropyl ether, methyl tent-butyl ether, dioxane, tetrahydrofuran and the like; esters such as ethyl acetate, isopropyl acetate and the like; hydrocarbon such as toluene, n-heptane, cyclohexane, xylene; polar aprotic solvents such as dimethylformamide, dimethyl sulfoxide, N-methylpyrrolidone or mixture thereof.

In an embodiment, 3-morpholino-1-(4-(2-oxopiperidin-1-yl)phenyl)-5,6-dihydropyridin-2(1H)-one of Formula VI can be prepared without isolating compound of Formula V.

According to present invention, step (d) involves condensation of 3-morpholino-1-(4-(2-oxopiperidin-1-yl)phenyl)-5,6-dihydropyridin-2(1H)-one of Formula VI with alkyl- (Z)-2-halo-2-(2-(4-methoxyphenyl)hydrazono)acetate of Formula VII, wherein $X_1$ is selected from chloro, bromo, iodo and Ak is H, $C_1$-$C_6$ alkyl group, which can be carried out in the presence of suitable base and solvent; followed by treatment with suitable acid to give alkyl-1-(4-methoxyphenyl)-7-oxo-6-(4-(2-oxopiperidin-1-yl)phenyl)-4,5,6,7-tetrahydro-1H-pyrazolo[3,4-c]pyridine-3 carboxylate of Formula VIII.

The suitable base used for above reaction is selected from inorganic or organic base. The inorganic base is selected from the group comprising of alkali metal or alkaline earth metal carbonates, bicarbonates, hydroxides, amides and the like, wherein the alkali metal and alkaline earth metal is selected from lithium, sodium, potassium, magnesium, calcium, cesium, barium and the like. The organic base is selected from the group comprising of triethylamine, diisopropylamine, diisopropylethylamine, 1,4-diazabicyclo[2.2.2]octane, 1,8-diazabicyclo[5.4.0]undec-7-ene, piperidine, pyridine N-methyl morpholine N,N-dimethylbenzylamine, picoline, lutidine and the like.

The suitable solvent for condensation is selected from the group comprising of chlorinated hydrocarbons such as methylene chloride, chloroform and the like; polar aprotic solvents such as dimethylformamide, dimethyl sulfoxide, N-methylpyrrolidone; non polar solvent selected from the group comprising of toluene, xylene, hexane, heptane, cyclohexane, cyclopentane, ethyl acetate, monochlorobenzene or mixture thereof.

Suitable acid used for the reaction is selected from the group comprises of inorganic acid or organic acid wherein the inorganic acid is selected from hydrochloric acid, hydrobromic acid, hydrofluoric acid and the like; or organic acid selected from ascorbic acid, formic acid, oxalic acid, lactic acid and citric acid, methane sulfonic acid, p-toluene sulphonic acid, trifluoroacetic acid and the like or suitable mixtures thereof. The acid is used as aqueous solution or in anhydrous form.

In an embodiment compound of Formula VII can be ethyl (Z)-2-chloro-2-(2-(4-methoxyphenyl)hydrazono)acetate of Formula VIIa.

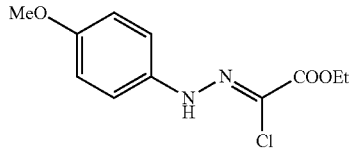

Formula VIIa

In an embodiment, 3-morpholino-1-(4-(2-oxopiperidin-1-yl)phenyl)-5,6-dihydropyridin-2(1H)-one compound of Formula VI reacts with alkyl-(Z)-2-halo-2-(2-(4-methoxyphenyl)hydrazono)acetate of Formula VII followed by in-situ treatment with suitable acid to give alkyl-1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate compound of Formula VIII.

According to the present invention, step (e) involves amidation of alkyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate of Formula VIII which can be carried out using formamide in presence of base and solvent to give Apixaban of Formula I.

The suitable base used for above reaction is selected from metal alkoxide, metal hydride, metal amide, organo metallic base or ammonia (aqueous or gas); wherein the metal alkoxide is selected from alkali metal or alkaline earth metal salt of alcohols, preferably the alkali metal and alkaline earth metal is selected from a group comprising of lithium, sodium, potassium, magnesium, calcium, cesium, barium and alcohol is selected from methanol, ethanol, propanol, butanol, pentanol or metal hydride, wherein metal amide is selected from sodium hydride, potassium hydride, calcium hydride and the like or metal amide wherein the metal amide is selected from alkali or alkaline earth metal amide of lithium, sodium, potassium, calcium and the like or organo metallic base wherein the organo metallic base is selected from n-butyl lithium, Grignard reagent and dialkyl copper lithium and the like.

The suitable solvent for amidation is selected from the group comprising of ethers such as, dioxane, tetrahydrofuran and the like; polar aprotic solvents such as dimethylformamide, dimethyl sulfoxide, N-methylpyrrolidone and the like; or mixture thereof.

The isolation of Apixaban can be optionally carried out by addition of a solvent selected from the group comprising of alcohols such as methanol, ethanol, propanol, isopropanol and butanol and the like; chlorinated hydrocarbons such as methylene chloride, chloroform and the like; ethers such as diisopropyl ether, methyl tent-butyl ether, dioxane, tetrahydrofuran and the like; esters such as ethyl acetate, isopropyl acetate butyl acetate and the like, polar aprotic solvents such as dimethylformamide, dimethyl sulfoxide, N-methylpyrrolidone and the like; and water or mixture thereof.

According to the present invention, step (f) comprises optionally purification of Apixaban by recrystallizing or slurring in suitable solvent selected from the group comprising alcohols such as methanol, ethanol, propanol, isopropanol and butanol and the like; ketones such as acetone, ethyl methyl ketone, diethyl ketone, methyl isobutyl ketone, and the like; chlorinated hydrocarbons such as methylene chloride, chloroform and the like; ethers such as diisopropyl ether, methyl tert-butyl ether and the like; esters such as ethyl acetate, isopropyl acetate and the like and water or mixture thereof.

In an embodiment pure Apixaban obtained according to the present invention, is having purity more than 99%.

In another aspect, the present invention is directed to novel compound of Formula Vb:

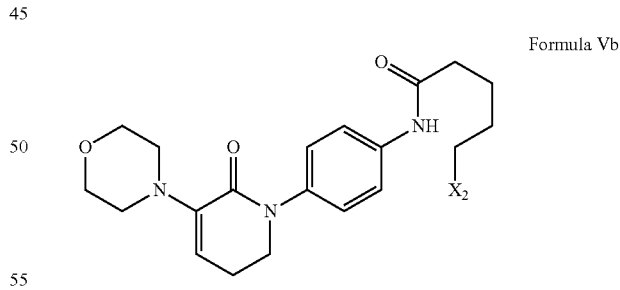

Formula Vb wherein, $X_2$ is selected from leaving group such as, bromo, iodo, mesylate, substituted or unsubstituted phenyl sulfonate and the like.

In one embodiment, the present invention discloses the novel compound of 5-bromo-N-(4-(5-morpholino-6-oxo-3,6-dihydropyridin-1(2H)-yl)phenyl)pentanamide of Formula Va characterized by:

$^1$H NMR (400 MHz, CDCl$_3$) : δ 8.19 (1H, s, N—H), δ 7.42 (2H, d, $J_o$=8.4 Hz, Ar—H), δ 7.19 (2H, d, $J_o$=8.8 Hz, Ar—H), δ 5.66 (1H, t, $J_o$=4.6 Hz), δ 3.83-3.80 (m, 4H, —CH$_2$—O—CH$_2$—), δ 3.75-3.72 (m, 2H, —N—CH$_2$—

CH$_2$—CH—), δ 2.91-2.84 (m, 6H, —CH$_2$—N—CH$_2$— and —CH$_2$—Br), δ 2.38-2.35 (m, 4H, —N—CH$_2$—CH$_2$—CH— and Br—CH$_2$—CH$_2$—CH$_2$—CH$_2$—), δ 1.95-1.85 (m, 4H, Br—CH$_2$—CH$_2$—CH$_2$—CH$_2$—).

IR (KBr, cm$^{-1}$): 3302 (N—H str), 2935, 2585 and 2810 (C—H aliphatic), 1683 and 1649 (C═O str.), 1620 (aliphatic C═C), 1537 and 1517 (aromatic C═C), 1265 (C—N str.), 1112, 1072 and 1037 (C—O str), 839 and 781 (Ar—H, aromatic bending).

MS/ESI: 436.16 (M+), 438.17 (M+2)

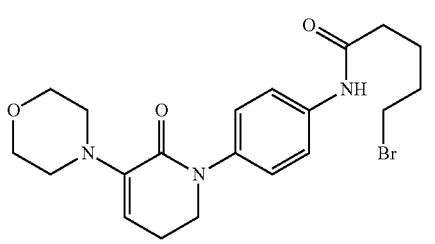

Formula Va

In another embodiment, the present invention is directed to novel compound 5-bromo-N-(4-(5-morpholino-6-oxo-3,6-dihydropyridin-1(2H)-yl)phenyl)pentanamide of Formula Va used as intermediate for the preparation of Apixaban.

In still another embodiment, the present invention is directed to substantially pure 5-bromo-N-(4-(5-morpholino-6-oxo-3,6-dihydropyridin-1(2H)-yl)phenyl)pentanamide of Formula Va.

In another embodiment, the present invention is directed to process for the preparation of 5-bromo-N-(4-(5-morpholino-6-oxo-3,6-dihydropyridin-1(2H)-yl)phenyl)pentanamide of Formula Va by reacting 3-morpholino-1-(4-aminophenyl)-5,6-dihydropyridin-2(1H)-one of Formula III with 5-bromopenatanoyl chloride in the presence of suitable base and solvent.

In another aspect, the present invention is directed to process for the preparation of compound of Formula Vb by reacting 3-morpholino-1-(4-aminophenyl)-5,6-dihydropyridin-2(1H)-one of Formula III with compound of Formula IV in the presence of base and solvent, wherein X$_1$ is selected from chloro, bromo, iodo or alkyl carboxy, wherein alkyl is selected from ethyl, isobutyl, t-butyl and the like; X$_2$ is selected from leaving group such as bromo, iodo, mesylate, substituted or unsubstituted phenyl sulfonate and the like.

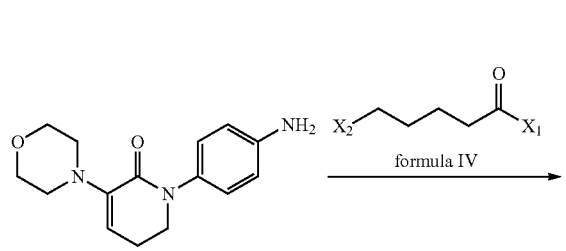

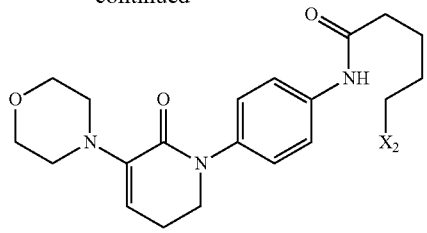

Formula Vb

The base is selected from organic or inorganic base, depending upon the class of solvent. The organic base is selected from the group comprising of triethylamine, diisopropylamine, diisopropylethylamine, piperidine, pyridine N-methyl morpholine N,N-dimethylbenzylamine, picoline, lutidine and the like; where the inorganic base is selected from the group comprising of alkali metal or alkaline earth metal carbonates, bicarbonates, hydroxides and the like, wherein the alkali metal and alkaline earth metal is selected from a group comprising of lithium, sodium, potassium, magnesium, calcium, cesium, barium and the like.

The suitable solvent is selected from the group comprising of chlorinated hydrocarbons such as methylene chloride, chloroform and the like; ethers such as diisopropyl ether, methyl tent-butyl ether, dioxane, tetrahydrofuran and the like; esters such as ethyl acetate, isopropyl acetate and the like, hydrocarbon such as toluene, n-heptane, cyclohexane, xylene; polar aprotic solvents such as dimethylformamide, dimethyl sulfoxide, N-methylpyrrolidone and water or mixture thereof.

EXAMPLES

The following examples are provided only to exemplify, but not to limit the scope of the invention.

Example 1

Synthesis of 3-morpholino-1-(4-aminophenyl)-5,6-dihydropyridin-2(1H)-one

To a mixture of 3-morpholino-1-(4-nitrophenyl)-5,6-dihydropyridin-2(1H)-one (5 g) and N-methylpyrrolidone (50 mL) 5% Pd/C (0.5 g) was added and the reaction mass was hydrogenated under pressure. After completion of the reaction, ethyl acetate (50 mL) was added to reaction mass. Further reaction mass was concentrated under vacuum, diluted with methanol (25 mL), filtered and dried to obtain title compound.
Yield 4.2 gm Example 1A Synthesis of 3-morpholino-1-(4-aminophenyl)-5,6-dihydropyridin-2(1H)-one A mixture of 3-Morpholin-4-yl-1-(4-nitro-phenyl)-5,6-dihydro-1H-pyridin-2-one (10 g, 0.0329 mol), ethanolamine (0.99 mL) and Raney Ni (2.0 g) was taken in methanol (100 mL) and stirred under hydrogen pressure in an autoclave at ambient temperature for 8 h. The reaction mixture was diluted with DCM (100 mL) and the catalyst was filtered off. The resulting filtrate was concentrated under reduced pressure at 45° C. to obtain solid, which was triturated with ethyl acetate, filtered and then dried under vacuum at 50-60° C. to obtain title compound as an off-white solid.
Yield: 95%
Purity: 98.9%

Example 1B

Synthesis of 3-morpholino-1-(4-aminophenyl)-5,6-dihydropyridin-2(1H)-one

A mixture of 3-Morpholin-4-yl-1-(4-nitro-phenyl)-5,6-dihydro-1H-pyridin-2-one (5 g, 0.0165 mol) and Raney Ni (1.0 g) was taken in methanol (50 mL) and stirred under hydrogen pressure in a Parr hydrogenator at ambient temperature for 8 h. The mixture was diluted with DCM (50 mL) at room temperature. The catalyst was filtered off and the filtrate was then concentrated under vacuum at 45° C. to get solid residue which was triturated with ethyl acetate (35 mL), filtered, and then dried under vacuum at 50-60° C. to obtain title compound as an off-white solid.
Yield: 62%
Purity: 87.5%

Example 1C

Synthesis of 3-morpholino-1-(4-aminophenyl)-5,6-dihydropyridin-2(1H)-one

To a suspended mixture of 3-morpholin-4-yl-1-(4-nitro-phenyl)-5,6-dihydro-1H-pyridin-2-one (100 g, 0.329 mol) and Raney Ni (10 g) taken in methanol (1000 mL) was added hydrazine hydrate (82.57 g, 1.649 mol) at 55-60° C. The heating was continued for further 1 h. The reaction mixture was cooled to room temperature and diluted with DCM (1000 mL). The resulting mixture was filter to remove the catalyst and the filtrate was concentrated under reduced pressure. The resulting residue was triturated with ethyl acetate (500 mL) to obtain solid which was filtered and dried under vacuum at 40-45° C. to yield the title compound as an off-white solid.
Yield: 94.30%
Purity: 99.60%

Example 1C

Synthesis of 3-morpholino-1-(4-aminophenyl)-5,6-dihydropyridin-2(1H)-one

A suspended mixture of 3-Morpholin-4-yl-1-(4-nitro-phenyl)-5,6-dihydro-1H-pyridin-2-one (40 g, 0.132 mol) and 5% Pd—C (2 g) was taken in N-methyl pyrrolidone (400 mL) and was hydrogenated under hydrogen atmosphere in autoclave at room temperature. After completion of reaction, the catalyst was filtered off, and the filtrate was diluted with water (400 ml) and extracted with DCM. The organic layer was separated and washed with water (3×100 mL). The DCM layer was concentrated under reduced pressure to obtain solid which was triturated with methyl tertiary butyl ether (200 mL), filtered and dried under vacuum at 40-45° C. for 8 h to obtain title compound as an off-white solid.
Yield: 70%
Purity: 98.89%

Example 1D

Synthesis of 3-morpholino-1-(4-aminophenyl)-5,6-dihydropyridin-2(1H)-one

To a suspended mixture of 3-Morpholin-4-yl-1-(4-nitro-phenyl)-5,6-dihydro-1H-pyridin-2-one (20 g, 0.066 mol) and ammonium formate (14.56 g, 0.231 mol) taken in methanol (200 mL), was added 5% Pd/C (1.2 g). The resulting mixture was heated at 35-40° C. under stirring for 3 h. The mixture was then cooled to room temperature and diluted with DCM (100 mL) under stirring. The resulting mixture was filter to remove the catalyst and the filtrate was concentrated under reduced pressure. The obtained residue was then dissolved in DCM (100 mL) and washed with water (2×50 mL). The organic layer was concentrated under reduced pressure at 40° C., triturated with methyl tertiary butyl ether (50 mL) at 25-30° C. The solid was filtered and dried under vacuum at 40-45° C. for 6-8 h to yield the title compound as an off-white solid.
Yield: 80%
Purity: 98.89%

Example 2

Synthesis of 5-bromo-N-(4-(5-morpholino-6-oxo-3,6-dihydropyridin-1(2H)-yl)phenyl)pentanamide To a mixture of 1-(4-aminophenyl)-3-morpholino-5,6-dihydropyridin-2(1H)-one of (2.0 g) and tetrahydrofuran was added 40% aq. $K_2CO_3$ (5.0 mL). Further to the reaction mass, 5-bromovaleryl chloride (1.75 g diluted in 10 mL tetrahydrofuran) was added at 0-5° C. and stirred the reaction mass for 30 minutes to 1 hours. After completion of reaction, tetrahydrofuran was removed under vacuum, diluted with water (20 mL), filtered and dried to obtain title compound.
Yield 2.9 g

Example 2A

Synthesis of 5-bromo-N-(4-(5-morpholino-6-oxo-3,6-dihydropyridin-1(2H)-yl)phenyl)pentanamide An ice-cold mixture of 1-(4-aminophenyl)-3-morpholino-5,6-dihydropyridin-2(1H)-one (2.0 g, 7.3 mmol) and aqueous potassium carbonate solution (prepared by dissolving 1.75 g of potassium carbonate in 5 ml water) was taken in THF (30 mL). To the resulting mixture, a solution of 5-bromovaleryl chloride (1.75 g, 8.7 mmol) in THF (10 mL) was added slowly at 0-5° C. The resulting mixture was stirred at the same temperature till completion. The solvent was evaporated off under vacuum at 40° C. The resulting residue obtained was stirred with water at room temperature, filtered and dried to obtain the title compound as pale-yellow solid.
Yield: 90.8%
Purity: 96.59%

Example 2B

Synthesis of 5-chloro-N-(4-(5-morpholino-6-oxo-3,6-dihydropyridin-1(2H)-yl)phenyl)pentanamide 1-(4-Aminophenyl)-3-morpholino-5,6-dihydropyridin-2(1H)-one (14.3 g, 0.0523 mol) and triethylamine (10.59 g, 0.105 mol) was taken in dichloromethane (143 mL). To the resulting mixture, 5-chlorovaleryl chloride (9.73 g, 0.0628 mol) was added under stirring at room temperature. After completion of the reaction, the reaction mass was quenched with water. The organic layer was separated, washed with water and concentrated under reduced pressure to obtain solid which was triturated with methyl tertiary butyl ether (71.5 mL). The resulting solid was filtered, washed with methyl tertiary butyl ether and dried under vacuum at 45° C. for 8 h to obtain title compound as off white solid.

Yield: 95.56%

Purity 98.6%

Example 3

Synthesis of 3-morpholino-1-(4-(2-oxopiperidin-1-yl)phenyl)-5,6-dihydropyridin-2(1H)-one To a mixture of 5-bromo-N-[4-(5-morpholino-6-oxo-3,6-dihydropyridin-1(2H)-yl)phenyl]pentanamide (2.5 g) and tetrahydrofuran (37.5 mL), was added sodium methoxide (30% dissolved in 15 mL tetrahydrofuran) and stirred the reaction mass for 2 hours at 25-30° C. After completion of reaction, 1% aq. glacial acetic acid solution (5.0 mL) was added at 25-30° C. and stirred for 10-15 minutes. The reaction mass was concentrated under vacuum and added water (12.5mL) followed by addition of methylene dichloride (37.5mL). Further reaction mass was stirred and separated the layers. The methylene dichloride layer was concentrated under vacuum to obtain title compound.

Yield 1.9 g

Example 3A

Synthesis of 3-morpholino-1-(4-(2-oxopiperidin-1-yl) phenyl)-5, 6-dihydropyridin-2(1H)-one 5-Bromo-N-[4-(5-morpholino-6-oxo-3,6-dihydropyridin-1(2H)-yl)phenyl]pentanamide (2.5 g, 5.7 mmol) was taken in THF. The resulting solution was stirred and cooled to 0-5° C. followed by addition of a solution of sodium methoxide (0.77 g, 4.2 mmol in THF (15 mL). The resulting mixture was stirred for 1 h and then warmed to room temperature. The resulting mixture was further stirred for 2 h. After completion of the reaction, the reaction mass was quenched with 1% glacial acetic acid solution (5 mL) and concentrated under reduced pressure at 40° C. To the residue, a mixture of water (12.5 mL) and DCM (37.5 mL) was added. The organic layer was evaporated under vacuum to obtain title compound as an off-white solid.

Yield: 93.32%

Purity: 92.37%

Example 3B

Synthesis of 3-morpholino-1-(4-(2-oxopiperidin-1-yl)phenyl)-5,6-dihydropyridin-2(1H)-one A suspended mixture of 5-chloro-N-[4-(5-morpholino-6-oxo-3,6-dihydropyridin-1(2H)-yl)phenyl]pentanamide (19.40 g, 0.0495 mol) and powdered KOH (5.55 g, 0.099 mol) was taken in dichloromethane (194 mL) and was refluxed for 4 h. The reaction mixture was cooled to room temperature and quenched with water (97 mL). The organic layer was washed with water and concentrated to dryness. The residue obtained was triturated with methyl tertiary butyl ether (97 mL) and the resulting solid was filtered, washed with methyl tertiary butyl ether and dried under vacuum to obtain the title compound as an off-white solid.

Yield: 94.99%

Purity: 98.35%

Example 4

Synthesis of Ethyl 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxylate To a mixture of ethyl (Z)-2-chloro-2-[2-(4-methoxyphenyl)hydrazono]acetate (1.58 g) and toluene (30 ml) was added triethylamine (1.13 g) and stirred for 30 minutes. Further to the reaction mass added 3-morpholino-1-[4-(2-oxopiperidin-1-yl)phenyl]-5,6-dihydropyridin-2(1H)-one (2.0 g) and reaction temperature was raised to 90° C. and stirred for 6 hours. After completion of reaction, added 1N hydrochloric acid (20 mL) to the reaction mass and stirred for 2-3 hours. The reaction mass was concentrated under vacuum, added water (150 mL) and stirred for 1-2 hours. The reaction mass was filtered, dried to obtain title compound.

Yield 2.24 g

Example 4A

Synthesis of Ethyl 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxylate 3-Morpholino-1-[4-(2-oxopiperidin-1-yl)-phenyl]-5,6-dihydropyridin-2(1H)-one (16.7 g, 0.047 mol) and ethyl (Z)-2-chloro-2-[2-(4-methoxyphenyl)hydrazine]acetate (16.89 g, 0.06582 mol) was taken in toluene (167 mL) and was stirred. To the resulting mixture, triethylamine (14.27 g, 0.1415 mol) was added drop wise at room temperature. The mixture was heated to 85-90° C. and stirred 2 h. After completion of the reaction, the solvents were distilled off under vacuum at 45-50° C. The resulting residue was dissolved in ethyl acetate (83.5 mL) and was treated with IPA-HCl (15%) at room temperature for 2 h. The reaction mixture was concentrated under vacuum. The heterogeneous reaction mass was cooled to room temperature and then filtered. The resulting solid was suspended in water (83.5 mL), stirred at room temperature for 2 h, filtered and dried under vacuum at 50-55° C. to obtain title compound as light-yellow powder.

Yield: 77.12%

Purity: 96.8%

Example 5

Synthesis of 1-(4-Methoxyphenyl)-7-oxo-6-[4-(2-oxopiperidin-1-yl)phenyl]-4,5,6,7-tetrahydro-1H-pyrazolo[3,4-c]pyridine-3-carboxamide (Apixaban)

To a mixture of ethyl 1-(4-methoxyphenyl)-7-oxo-6-[4-(2-oxopiperidin-1-yl) phenyl]-4,5,6,7-tetrahydro-1H-pyrazolo[3,4-c]pyridine-3-carboxylate (0.5 g) and DMF (1.85 mL) added formamide solution (0.32 g diluted in 1.0 mL DMF) at 25-30° C. The reaction mass was cooled to −5 to 0° C., added sodium methoxide (0.084 g diluted in 1 mL of DMF) and stirred for 30 min. The reaction mass was raised to 25-30° C. and stirred for 1-2 hours. To the reaction mass water (50.0 mL) was added and stirred for 1-2 hours. Further reaction mass was filtered, dried under vacuum to obtain Apixaban.
Yield 0.40 g Example 5A 1-(4-Methoxyphenyl)-7-oxo-6-[4-(2-oxopiperidin-1-yl)phenyl]-4,5,6,7-tetrahydro-1H-pyrazolo[3,4-c]pyridine-3-carboxamide To a stirred solution of ethyl 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxylate, (32.16 g, 0.06587 mol) in formamide (160.8 mL), a solution of 30% sodium methoxide (47.44 g, 0.26349 mol) was added at room temperature. The resulting mixture was stirred for 2 h. After completion of the reaction, the reaction mixture was diluted with water and stirred at room temperature for 4 h. The precipitated solid was filtered, washed with water and dried under vacuum at 50-55° C. for 12 h to obtain the title compound.
Yield: 90.38%
Purity: 93.40%

Example 6

Synthesis of Pure 1-(4-Methoxyphenyl)-7-oxo-6-[4-(2-oxopiperidin-1-yl)phenyl]-4,5,6,7-tetrahydro-1H-pyrazolo[3,4-c]pyridine-3-carboxamide A suspension of 1-(4-Methoxyphenyl)-7-oxo-6-[4-(2-oxopiperidin-1-yl)phenyl]-4,5,6,7-tetrahydro-1H-pyrazolo[3,4-c]pyridine-3-carboxamide (2 g) in a mixture of dichloromethane (30 mL) and methanol (30 mL) was heated to reflux under stirring for 30 minutes to obtain a clear solution. The solution was cooled to 30° C. and activated carbon (0.10 g) was added. The mixture was stirred. The resulting mixture was cooled to room temperature, filtered through hyflo and the hyflo bed was washed with a solvent mixture dichloromethane and methanol. The resulting filtrate was concentrated under reduced pressure and IPA (30 mL) was added, heated to 80-85° C. for 12 h, cooled to room temperature and stirred for 2 h. The resulting white solid was filtered, washed with IPA (2×4 mL) and dried under vacuum at 50° C. for 8 h to obtain pure Apixaban.
Yield: 84%
Purity: 97.53%

We claim:
1. A process for preparation of Apixaban of Formula I, comprising the steps of:
   a) reducing 3-morpholino-1-(4-nitrophenyl)-5,6-dihydropyridin-2(1H)-one of Formula II in presence of reducing agent and solvent to give 3-morpholino-1-(4-aminophenyl)-5,6-dihydropyridin-2(1H)-one of Formula III;

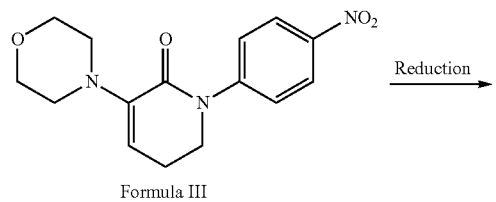

Formula III

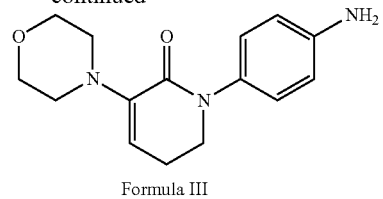

Formula III b) reacting 3-morpholino-1-(4-aminophenyl)-5,6-dihydropyridin-2(1H)-one of Formula III with compound of formula IV in presence of base and solvent to give compound of Formula V;

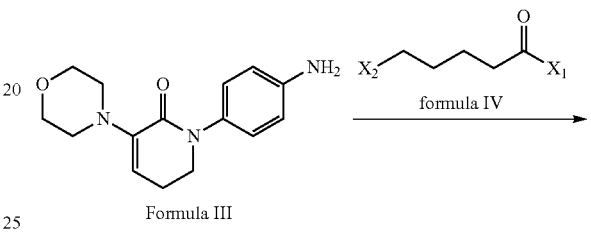

Formula III formula IV

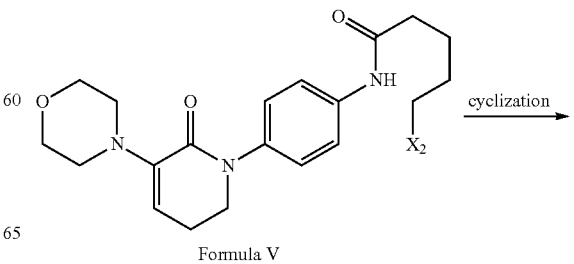

Formula V wherein, $X_1$ is selected from chloro, bromo, iodo or alkyl carboxy, wherein alkyl is selected from ethyl, isobutyl, t-butyl and $X_2$ is selected from leaving group such as, chloro, bromo, iodo, mesylate, substituted or unsubstituted phenyl sulfonate;

c) cyclizing compound of Formula V in the presence of base and solvent to give 3-morpholino-1-(4-(2-oxopiperidin-1-yl)phenyl)-5,6-dihydropyridin-2(1H)-one of Formula VI;

Formula V cyclization

-continued

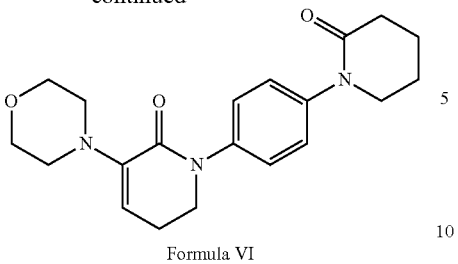

Formula VI d) condensing 3-morpholino-1-(4-(2-oxopiperidin-1-yl) phenyl)-5,6-dihydropyridin-2(1H) one of Formula VI with alkyl-(Z)-2-halo-2-(2-(4-methoxyphenyl)hydrazono)acetate of Formula VII, wherein $X_1$ is selected from chloro, bromo, iodo and Ak is $C_1$-$C_6$ alkyl; in presence of base and solvent, followed by treatment with acid to give alkyl 1-(4-methoxyphenyl)-7-oxo-6-(4-(2-oxopiperidin-1-yl)phenyl)-4,5,6,7-tetrahydro-1H-pyrazolo [3,4-c] pyridine-3-carboxylate of Formula VIII;

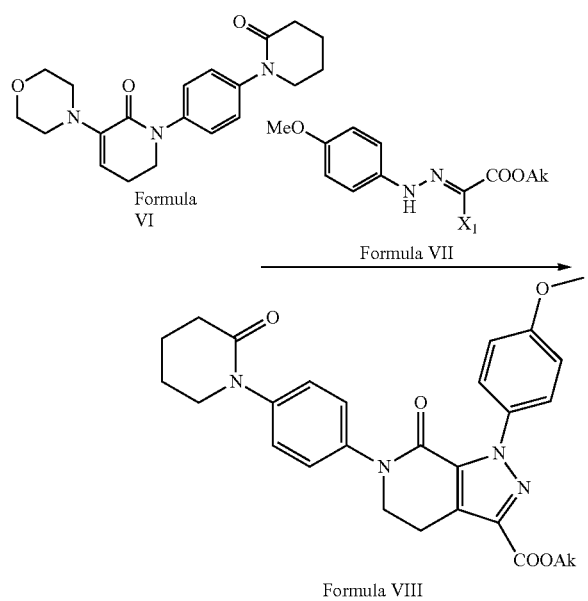

e) amidating the compound of Formula VIII using using formamide in presence of base and solvent to give Apixaban of Formula I;

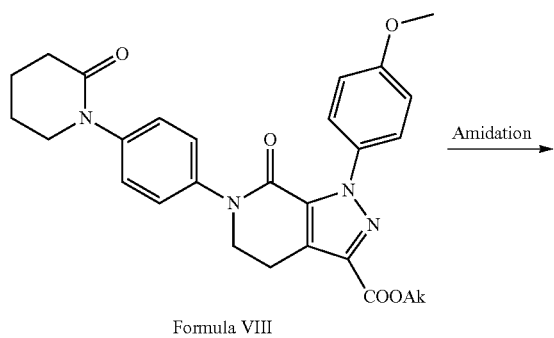

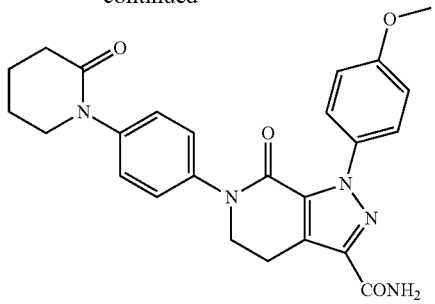

Apixaban
Formula I f) optionally purifying Apixaban of Formula I.

2. The process according to claim 1, wherein in step (a) the reducing agent is selected from the group comprising of hydrogen in presence of metal catalysts such as Pd/C, Pt/C, Raney Ni; optionally in presence of ethanolamine or hydrazine hydrate, transfer hydrogenation using ammonium formate, formic acid in presence of metal catalyst such as Pd/C, Pt/C; Fe/HCl, Zn/HCl, Sn/HCl, or pyridinium zinc complex; sodium borohydride, sodium cyanoborohydride, sodium triacetoxyborohydride, trihalosilanes, diisobutylaluminium hydride (DIBAL), lithium triethylborohydride, lithium tri-sec-butyl borohydride (L-selectride), trialkylsilanes optionally in combination with trifluoroacetic acid.

3. The process according to claim 1, wherein in step (a) the solvent used for reduction is selected from the group comprising of alcohols such as methanol, ethanol, propanol, isopropanol and butanol; chlorinated hydrocarbons such as methylene chloride, chloroform; ethers such as diisopropyl ether, methyl tert-butyl ether, dioxane, tetrahydrofuran; esters such as ethyl acetate, isopropyl acetate; polar aprotic solvents such as dimethylformamide, dimethyl sulfoxide, N-methylpyrrolidone and water or mixture thereof.

4. The process according to claim 1, wherein in step (b) the base is selected from inorganic or organic base; wherein the inorganic base is selected from the group comprising of alkali metal or alkaline earth metal carbonates, bicarbonates, hydroxides, preferably the alkali metal and alkaline earth metal of lithium, sodium, potassium, magnesium, calcium, cesium and barium; or organic base is selected from the group comprising of triethylamine, diisopropylamine, diisopropylethylamine, piperidine, pyridine N-methyl morpholine N, N-dimethylbenzylamine, picoline and lutidine.

5. The process according to claim 4, wherein in step (b) the solvent is selected from the group comprising of chlorinated hydrocarbons such as methylene chloride, chloroform; ethers such as diisopropyl ether, methyl tert-butyl ether, dioxane, tetrahydrofuran; esters such as ethyl acetate, isopropyl acetate; hydrocarbon such as toluene, n-heptane, cyclohexane, xylene; polar aprotic solvents such as dimethylformamide, dimethyl sulfoxide, N-methylpyrrolidone or mixture thereof.

6. The process according to claim 1, wherein in step (c) the solvent is selected from the group comprising chlorinated hydrocarbons such as methylene chloride, chloroform; ethers such as diisopropyl ether, methyl tert-butyl ether, dioxane, tetrahydrofuran; esters such as ethyl acetate, isopropyl acetate; hydrocarbon such as toluene, n-heptane, cyclohexane, xylene; polar aprotic solvents such as dimethylformamide, dimethyl sulfoxide, N-methylpyrrolidone or mixture thereof.

7. The process according to claim 6, wherein in step (c) the base is selected from inorganic or organic base; wherein the inorganic base is selected from the group comprising of alkali metal or alkaline earth metal carbonates, bicarbonates, hydroxides, amide, preferably the alkali metal and alkaline earth metal of lithium, sodium, potassium, magnesium, calcium, cesium, barium; or organic base is selected from the group comprising of triethylamine, diisopropylamine, diisopropylethylamine, 1,4-diazabicyclo[2.2.2]octane, 1,8-Diazabicyclo[5.4.0]undec-7-ene piperidine, pyridine N-methyl morpholine N, N-dimethylbenzylamine, picoline and lutidine.

8. The process according to claim 1, wherein in step (d) alkyl-(Z)-2-halo-2-(2-(4-methoxyphenyl) hydrazono)acetate of Formula VII is selected from ethyl (Z)-2-chloro-2-(2-(4-methoxyphenyl)hydrazono)acetate of Formula VIIa.

9. The process according to claim 1, wherein in step (d), base is selected from inorganic or organic base; wherein the inorganic base is selected from the group comprising of alkali metal or alkaline earth metal carbonates, bicarbonates, hydroxides, amides, wherein the alkali metal and alkaline earth metal is selected from lithium, sodium, potassium, magnesium, calcium, cesium, barium; or the organic base is selected from the group comprising of triethylamine, diisopropylamine, diisopropylethylamine, 1,4-diazabicyclo[2.2.2]octane, 1,8-diazabicyclo[5.4.0]undec-7-ene piperidine, pyridine N-methyl morpholine N, N-dimethylbenzylamine, picoline and lutidine.

10. The process according to claim 1, wherein in step (d) the solvent is selected from the group comprising of methanol, ethanol, propanol, isopropanol and butanol; chlorinated hydrocarbons such as methylene chloride, chloroform; ethers such as diisopropyl ether, methyl tert-butyl ether, dioxane, tetrahydrofuran; esters such as ethyl acetate, isopropyl acetate; hydrocarbon such as toluene, n-heptane, cyclohexane, xylene; polar aprotic solvents such as dimethylformamide, dimethyl sulfoxide, N-methylpyrrolidone and water or mixture thereof.

11. The process according to claim 1, wherein in step (d) the acid is selected from inorganic acid such as hydrochloric acid, hydrobromic acid, hydrofluoric acid or organic acid selected from ascorbic acid, formic acid, oxalic acid, lactic acid, citric acid, methane sulphonic acid, p-toluene sulphonic acid or trifluoroacetic acid or suitable mixtures thereof.

12. The process according to claim 1, wherein in step (e) base is selected from metal alkoxide, metal hydride, metal amide, organo metallic base or ammonia (aqueous or gas); wherein the metal alkoxide is selected from alkali metal or alkaline earth metal salt of alcohols, preferably the alkali metal and alkaline earth metal is selected from a group comprising of lithium, sodium, potassium, magnesium, calcium, cesium, barium and alcohol is selected from methanol, ethanol, propanol, butanol, pentanol or metal hydride wherein the metal hydride is selected from sodium hydride, potassium hydride, calcium hydride or metal amide wherein the metal amide is selected from alkali or alkaline earth metal amide wherein the alkali metal and alkaline earth metal is selected from a group comprising of lithium, sodium, potassium, calcium or organo metallic base wherein the organo metallic base is selected from n-butyl lithium, Grignard reagent and dialkyl copper lithium.

13. The process according to claim 1, wherein in step (e) solvent is selected from the group comprising of ethers such as, dioxane, tetrahydrofuran; or polar aprotic solvents such as dimethylformamide, dimethyl sulfoxide, N-methylpyrrolidone; or mixture thereof.

* * * * *